United States Patent [19]

Phillips

[11] 4,042,350
[45] Aug. 16, 1977

[54] METHODS AND APPLICATIONS OF PREPARATIVE SCALE CHROMATOGRAPHY

[75] Inventor: Courtenay Stanley Goss Phillips, Oxford, England

[73] Assignee: National Research Development Corporation, London, England

[21] Appl. No.: 588,908

[22] Filed: June 20, 1975

[30] Foreign Application Priority Data

July 3, 1974 United Kingdom .............. 29491/74

[51] Int. Cl.² ............................................ B01D 15/08
[52] U.S. Cl. ......................................... 55/28; 55/67; 55/197
[58] Field of Search .................... 55/28, 67, 197, 267, 55/208; 210/198 C

[56] References Cited

U.S. PATENT DOCUMENTS

| | | | |
|---|---|---|---|
| 2,398,818 | 4/1946 | Turner | 55/197 |
| 2,893,955 | 7/1959 | Coggeshall | 55/67 X |
| 3,035,383 | 5/1962 | Sanford et al. | 55/67 |
| 3,043,127 | 7/1962 | De Ford et al. | 73/23.1 C |
| 3,057,183 | 10/1962 | De Ford | 55/67 X |
| 3,077,103 | 2/1963 | Heaton | 55/67 X |
| 3,225,521 | 12/1965 | Burow | 55/197 X |
| 3,865,562 | 2/1975 | Ayers et al. | 55/67 |

Primary Examiner—John Adee
Attorney, Agent, or Firm—Finnegan, Henderson, Farabow & Garrett

[57] ABSTRACT

A preparative scale chromatographic method in which a mixture is chromatographically fractionated on a sorbent material by the displacing action of a sorbate which is thermally displaced through the material by a heated zone advancing through the material to leave behind sorbent material substantially free of said sorbate. In an application of particular interest, at least one component of the mixture is produced by catalytic reaction of one or more thermally displaced sorbates induced by the heated zone of sorbent material.

10 Claims, 6 Drawing Figures

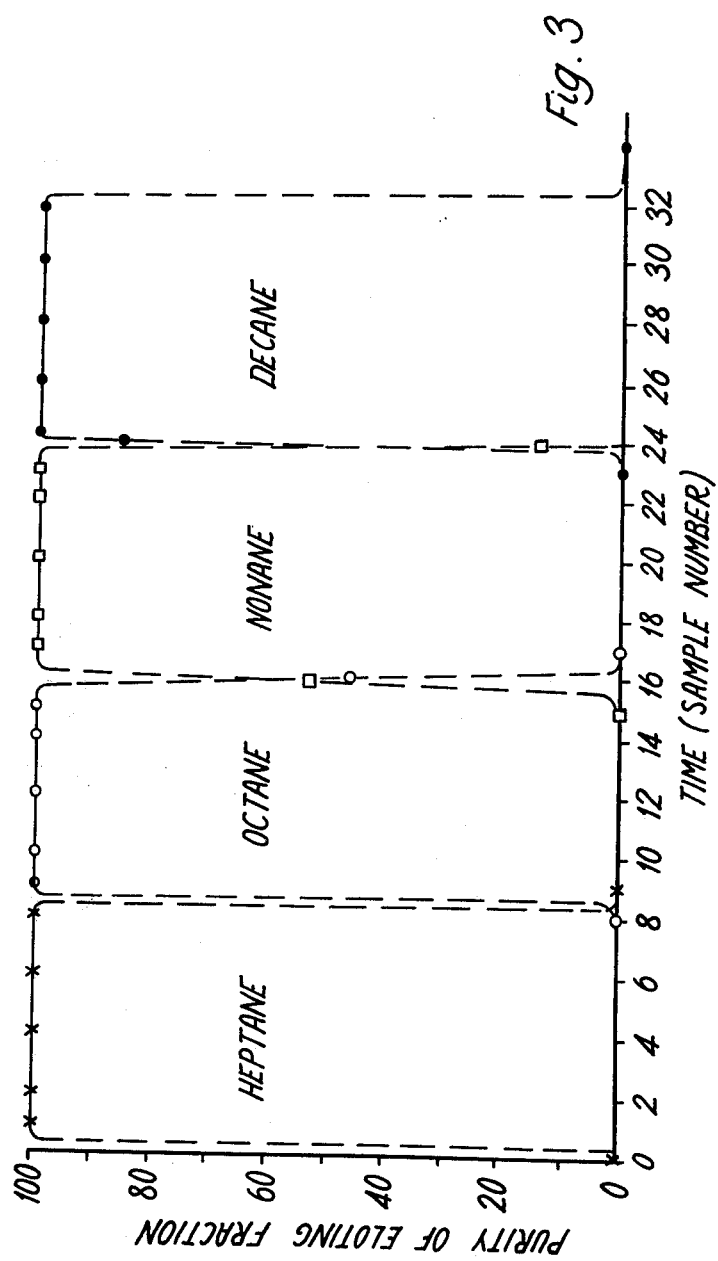

METHODS AND APPLICATIONS OF PREPARATIVE SCALE CHROMATOGRAPHY

This invention relates to methods and applications of preparative scale chromatography.

Numerous explorations have hitherto been made into the analytical and preparative scale applications of elution gas chromatography. The present invention is directed to applications of a different type of chromatography in which one component of a sorbate mixture on a sorbent material is displaced through the material to effect displacement and separation therefrom of a second component. For the purposes of this specification the latter method is called "displacement chromatography". Whilst the apparatus and method described in U.S. Pat. No. 2,398,818 appears to employ displacement chromatography it is not readily adapted for fractionation on a preparative scale and for continuous operation.

A method has now been found by means of which mixtures can be fractionated on a preparative scale.

Accordingly, the present invention comprises a preparative scale chromatographic method in which a mixture is chromatographically fractionated on a sorbent material by the displacing action of a sorbate which is thermally displaced through the material by a heated zone advancing through the material to leave behind sorbent material substantially free of said sorbate. The present invention may find application both purely separatively and, as hereinafter particularly described, as part of a method in which other processes operate.

In the method of the present invention, components of a sorbate mixture carried on a sorbent material are repeatedly displaced from the material into the vapour phase and resorbed therefrom on to the material as the heated zone moves along the material. The temperature within the heated zone along the direction of advancement is usually substantially uniform and is generally so controlled that in purely separative applications, the amount of the thermally displaced sorbate which falls within the zone is insignificant. Components of the sorbate mixture with differing affinities for the sorbent material are thereby separated into fractions, which adjoin each other on the material. The sorbate which is directly thermally displaced by advancement of the heated zone usually forms one component of the mixture to be fractionated. The latter sorbate moves through the sorbent material to displace the one or more other components of the mixture, and the most strongly sorbed of these other components in turn displaces less strongly sorbed components so that when displacement is complete, the components occupy adjacent regions on the sorbent material extending from the heated zone.

As the sorbent material left behind the heated zone on advancement thereof is substantially free from displacing sorbate, the present method enables high throughputs to be achieved. The sorbent material left behind the heated zone is available without further treatment for chromatographic separation. In a preferred mode of operation a plurality of heated zones is advanced through a mass (preferably a continuous mass) of sorbent material each effecting fractionation of a sorbate mixture in the path thereof. In this case the major portion of the sorbent material may be brought into use at one time.

It is highly desirable that the method of the present invention be capable of continuous operation. Particularly when a plurality of heated zones is produced in the sorbent material, the heating means associated with each heated zone may be movable, or the material may be movable relative to the heating means, in an endless path to displace sorbate from the material. In this case the container for the sorbent material, which is typically tubular, itself conveniently forms a loop or the major part thereof around which at least part of each heating means travels, the container being most simply toroidal in configuration although in situations where space saving is important, other configurations may be preferred. Such systems may be operated by continuously supplying starting material to the sorbent material near the inlet where it accumulates until a heated zone effects displacement towards the outlet thereby to fractionate the material. As the zone moves away from the inlet, further starting material is introduced and accumulates in the region thereof until a second heated zone approaches and effects displacement.

In an alternative system suitable for continuous operation, consecutive sections of the container are each associated with means for intermittently generating a heated zone to one end thereof and for moving the zone to the other end whereby movement of at least one of said zones effects displacement of sorbate in the path thereof into the next consecutive section. When the sorbate has been displaced from one section into the next, a heated zone generated at or near one end thereof is then moved along the section to continue displacement of the sorbate. Typically the heated zones are generated in each section and moved therealong in a synchronous manner.

In other systems, each heated zone generated in the region of the inlet moves through the sorbent material to the outlet region and fresh zones are intermittently generated in the inlet region. It will be appreciated that in such systems it may be necessary for heating means or part thereof moving from the outlet to the inlet to pass heating means moving in the opposite sense. This can be conveniently accomplished by providing heating means comprising a heating coil surrounding the tubular container or part thereof, and pairs of electrical conductors each pair mounted on a support member movable along the container. Each heated zone is produced by passing a current between each pair of conductors through one or more turns of the coil in contact therewith. By arranging for each pair of conductors to follow a separate path along the surface of the tubular container, the conductors can pass one another when moving in opposite senses.

Other types of heating means which may be preferred include induction heaters, which give rise to uniform radial temperatures in the sorbent material. The heaters are preferably annular to accommodate the tubular container on which they are conveniently mounted. Although it is convenient for the sorbent material to remain stationary and for the heaters to move, if so desired the sorbent material can instead be moved in relation to the heaters by appropriate movement of the tubular container.

It will be appreciated that in practice, the apparatus is provided with an inlet for starting material, and outlet means communicating with collection means for separating fractions. When a plurality of heaters is employed circulating around a loop each heater is so shaped that it can pass both inlet and outlet, which are generally provided with valves. The mixture to be separated is preferably continuously fed to the sorbent material through the inlet and accumulates in the region thereof until a heater, or a thermally displaced sorbate associated with a heater, approaches the mixture on the sorbent material and effects separation of the mixture by displacement.

The outlet usually communicates with means for diverting fractions displaced from the outlet into different collection vessels, which may be cooled to a low temperature to increase the degree of recovery. When the apparatus is operated without a flow of carrier gas and the separated fractions are sufficiently involatile, it may be unnecessary to provide cooling means to precipitate the products. The use of a carrier gas is however in general preferred because of the greater versatility in the application of the method to different fractionation problems. Gases such as nitrogen and air may be passed through the sorbent material and may be re-cycled for operational economy.

both absorbent and adsorbent materials may be used in the present invention. Absorbent materials may comprise substances which are liquid at the operating temperature in which liquid substances solid materials are dispersed, for example, metal compounds which can form complexes with the substances to be separated e.g. copper compounds for the separation of substituted pyridines. The solid materials provide sites for which components of the mixture to be separated compete.

Adsorbent materials include non-polar substances such as charcoal which can effect separations based largely on differences in boiling point and polar substances such as alumina and silica gel which are particularly effective in the separation of mixtures containing olefines, other polarisable molecules and polar molecules such as halogenated hydrocarbons. Substances which discriminate between components on the basis of different structural features thereof also find application, for example zeolites which sorb straight chain molecules to a far greater degree than branched chain molecules. The adsorbent materials may be further modified by the presence of other materials on the surface thereof. Alumina and silica for example may be modified by the incorporation of salts at the surface. When an olefin is to be fractionated from a mixture for example a surface of alumina/sodium chloride or alumina/cuprous chloride may be used advantageously. In some cases the sorbent material may not be homogenous, but comprise differing materials which combine to effect a particular separation.

It is not generally necessary to prepare a preparative scale column of sorbent material before the effectiveness thereof in fractionating a mixture can be assessed. A guide to the efficiency of separation can usually be obtained more rapidly by conducting beforehand elution gas chromatography of the mixture on an analytical-scale column. Excellent separation of two sorbates on a preparative scale can usually be effected when the ratio of retention times determined by analytical elution gas chromatograpy is 1.2:1 or more.

As hereinbefore indicated displacement of a sorbate mixture may be effected either directly by the action of a moving heated zone on the sorbate or by the action of a further sorbate which itself is displaced either directly or indirectly towards the sorbate mixture. Particularly when the mixture to be fractionated contains one or more thermolabile components, the recovery of which is desired, it is preferable for indirect displacement to be employed so that the mixture does not come into contact with a heated zone. In this case it may be necessary to add a further substance to the mixture which has a greater affinity for the sorbent material than any thermolabile component of the mixture so that the substance can act as a "thermal buffer substance" or as a part thereof between a heated zone and the labile sorbate.

The purity of fractions may often be considerably increased by the use of a buffer substance which separates two fractions on the sorbent material. The buffer substance is preferably selected so that any substance contaminating the product fractions can be readily separated therefrom by common chemical or physical methods such as selective absorption, adsorption or solution. By for example choosing an olefin as a buffer between two paraffins, the degree of separation between the paraffins can be greatly enhanced. After displacement from the outlet, the fractions can be treated, e.g. with sulphuric acid, to remove undesired olefin. As a further example, an acid can be selected to fall between two paraffins on the sorbent material and can be subsequently removed from the product fractions by solution in water.

The purity of fractions displaced from the column may if desired be monitored by provision of a small "bleed" at the outlet of the column communicating with an analytical gas chromatography apparatus.

As hereinbefore indicated the present invention may find application as part of a method in which other processes operate. The present invention is of especial interest when incorporated into catalytic processes.

For many years industrial catalytic processes have been conducted in three discrete stages:
1. catalytic reaction
2. separation of the products from each other and/or from the starting material, and
3. re-cycling of unused starting material.

It has now been found that stages 1 and 2 and in appropriate cases stage 3 can be conducted in one reactor with consequent economy in space, labour and time.

According to a further aspect of the present invention as hereinbefore defined, at least one component of the mixture is produced by catalytic reaction of one or more thermally displaced sorbates induced by the heated zone of sorbent material.

In practice a sorbate which is subjected to the catalytic action of the heated zone of sorbent material is thereby also thermally displaced through at least part of the sorbent material to effect displacement and fractionation of one or more other sorbates in the path thereof. The present method is particularly applicable to thermally induced catalytic reactions, such as decomposition or isomerisation, in which only one sorbate species reacts, but may also be applied to reactions in which two or more sorbate species react together catalytically.

The method of the present invention permits a variety of catalytic reactions to be controlled to yield desired products which may not be thermodynamically favoured. The method of the present invention is of value for example in a case in which a starting material is, in a conventional static system, catalytically convertible under the action of heat into an equilibrium mixture containing the starting material in addition to one or more products. If, in the present method, the catalytic sorbent material is chosen so that thermal contact between the heated zone and a reactive product is relatively reduced, reversionary reaction to the starting material may be obviated and the starting material may be totally converted to a product which can eventually be displaced from the sorbent material and recovered. In a typical case a reaction may be driven beyond its normal equilibrium position by selecting the catalytic sorbent material so that the starting material is sorbed more strongly than any reaction product and hence acts as a "buffer" interposed between the heated zone and the product or products, thus reducing or inhibiting heat-induced reversion. A starting material may for example be initially catalytically converted under the action of the heated zone to a mixture comprising one or more products and starting material. The product or products are displaced into a relatively cool region of the catalytic sorbent material adjacent the region containing the residual starting material. Movement of the heated zone progressively effects further catalytic conversion to product or products until the region containing the starting material becomes insignificant relative to that containing the product or products whereupon reaction ceases and the product or products are displaced from the catalytic sorbent material and may be recovered.

When one or more sorbate products are convertible (e.g. by isomerisation) to one or more sorbate products under the action of heat and the catalytic sorbent material, the present method may be employed to give substantial conversion to the sorbate having the least affinity for the sorbent material. For example, the starting material may be catalytically converted under the action of the heated zone to a mixture containing residual starting material and at least one product which is convertible to one or more other reaction products, the product being displaced into a cooler region of the catalytic sorbent material adjacent the starting material. The heated zone progressively converts the starting material into the latter product until an insignificant amount of starting material remains, the product (which next follows in the displacement sequence) is catalytically converted by the action of the heated zone and the product or products thereof displaced into the cooler regions. The process may be continued in cases where the products are interconvertible, until the least strongly sorbed product remains whereafter it may be recovered. The process may be alternatively operated so that a product which is more strongly sorbed than another product or products thereof is primarily produced. This may be achieved for example by locating a buffer substance before the desired product in the displacement sequence so that the product is not subject to further heat-induced reaction, or by providing heated zones so spaced apart that the desired product lies in the cooler region of the catalytic sorbent material therebetween. In the latter case the leading heated zone reverses any tendency for conversion of the adjacent desired product to further less strongly sorbed product under the effect of the following zone. The two zones generally move towards the outlet synchronously until the desired product is displaced therefrom. In this case it may be desirable for a buffer substance to be located before the desired product in the displacement sequence so that retrograde conversion of the latter product by the action of the heated zone thereon is inhibited and the product is obtained substantially free from the other sorbates into which it is convertible.

Particularly in the case wherein the products of catalytic conversion are capable of interaction together in the cooler regions of the catalytic sorbent material in advance of the heated zone, such interaction may if desired, be inhibited by means of a buffer substance located between products in the displacement sequence which are liable to interact. Such a buffer substance is generally introduced as an additive to the starting material or separately but in some cases may be derived from the starting material. The use of buffer substances generally gives rise to a further advantage in that greater separation and hence purity of the products can be thereby achieved, provided of course that any buffer contaminating a product displaced from the sorbent material is readily removable therefrom by simple chemical or physical processes such as selective absorption or solution. By for example choosing an olefin as a buffer between two paraffins, the degree of separation between the paraffins can be greatly enhanced. After displacement from the outlet, the fractions can be treated with sulphuric acid to remove undesired olefin. As a further example, an acid can be selected to fall between two paraffins and can be subsequently removed from the product fractions by solution in water.

The method of the present invention may be of value when reaction of a product or products in the relatively cool regions of the sorbent material is insignificant or alternatively when further reactions take place therein. Such further reactions may yield further products or further amounts of reactant undergoing catalytic conversion. The latter mode of operation is of particular value when a given catalytic reaction yields in addition to a desired first product other products (e.g. isomeric products) which can be recycled to yield further amounts of the first product. When thus operated the present method offers means by which such recycling can be carried out continuously in one reactor. In a typical case the starting material is catalytically converted initially into three or more products which are displaced to consecutive regions of the cooler catalytic sorbent material. Two products in adjacent regions react to regenerate starting material which moves into the region containing the residual starting material undergoing catalytic conversion under the action of the heated zone. In this manner all but one of the reactive products may be continuously recycled while the one product accumulates and may be recovered. By operating in this way reactions which yield only a small quantity of a desired product in static systems may be driven to effect substantially total conversion thereto. The present mode of operation is illustrated by the dehydrochlorination of 2-chlorobutane on a catalytic sorbent material such as surface modified alumina. 2-chlorobutane yields 1-butene, cis- and trans- 2-butene and hydrogen chloride on conventional dehydrochlorination in a static system. If in the present process the catalytic sorbent material is so chosen that the affinity of the sorbates for the sorbent material decreases in the order 2-chlorobutane, 1-butene, cis- and trans- 2-butene and hydrogen chloride, then hydrogen chloride will react with cis- and trans- 2-butene either sequentially if they lie in separate regions or simultaneously if they both lie in the same region, to regenerate 2-chlorobutane which undergoes further decomposition. 1-butene which at least initially does not contact and hence react with hydrogen chloride will thus accumulate and may be recovered. In such a process the regions separating the desired product, e.g. 1-butene, from a reactant, e.g. hydrogen chloride, may become insignificant towards the end of the reaction and the desired product may begin to react. This may be readily prevented by interposing a buffer substance in the displacement sequence immediately adjacent and to the rear of the desired product (in the above illustration between 1-butene and cis- and trans- 2-butene).

It will be appreciated that the catalytic sorbent material is so chosen that the desired displacement sequence is obtained. The sorbent material may be selected from those hereinbefore described and include gamma alumina, treated with a small percentage of potassium chloride the latter being particularly useful in the dehydrochlorination of chloroalkanes, gamma alumina treated with small amounts of platinum which is subsequently chlorinated at elevated temperatures with carbon tetrachloride, which latter material is useful in the isomerisation of paraffins, and gamma alumina treated with hydrogen fluoride which is useful in the isomerisation of alkenes.

The present invention finds particular application in the production of decomposition products, e.g. alkenes, or isomerisation products from chlorinated alkanes and in the production of relatively highly branched paraffins from less highly branched paraffins, e.g. n- paraffins.

Embodiments of the present invention will now be described by way of example only with reference to the accompanying drawings of which:

FIG. 3 shows a plot representing the fractionation of a mixture of n-paraffins into components.

EXAMPLE 1

Figure 1:
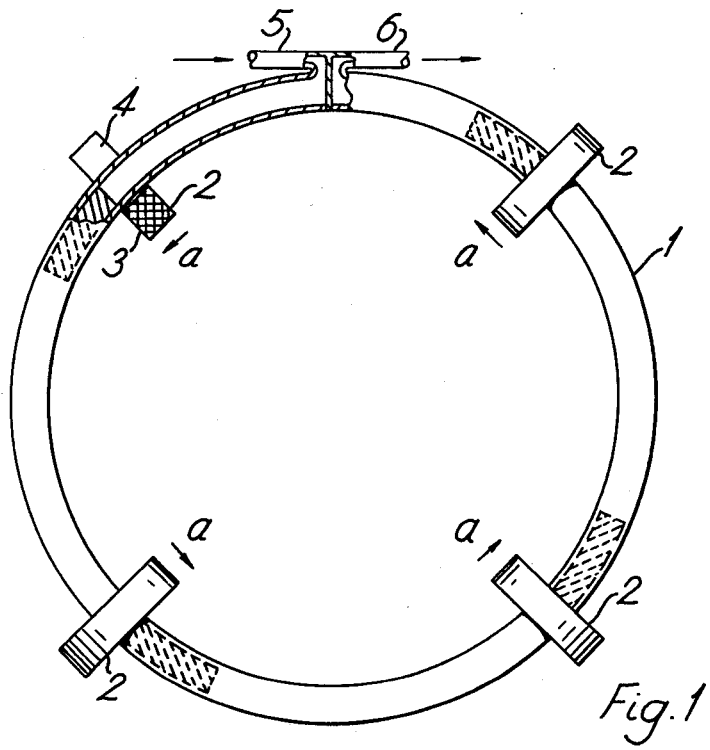
FIG. 1 represents diagrammatically apparatus for effecting fractionation of a mixture according to the present invention.
Figure 2:
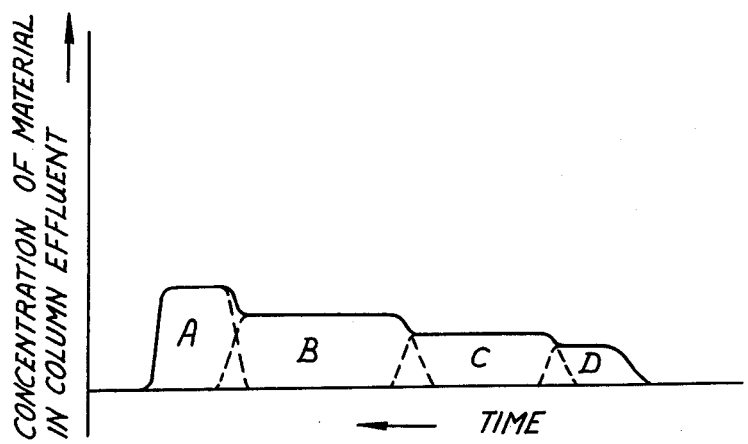
FIG. 2 shows a plot representing the fractionation of a typical four-component mixture.

Referring now to FIGS. 1 and 2, a toroidal tubular container 1 of a suitable chemically resistant material such as stainless steel carries four quasi annular heaters 2 each provided with resistance heating coils 3 and continuously movable by means not shown around the container in the direction indicated by the arrow a. Each heater is provided with a radial slot one wall of which 4 is shown in one heater, through which inlet and outlet manifolds 5, 6 can pass.

In operation, feed material is intermittently or continuously introduced to sorbent material (not shown) packed into the container, through the inlet manifold 5. A heater then approaches the feed material on the sorbent and effects separation thereof into components by displacement chromatography. In the steady state each heater is associated with a band of sorbate undergoing repeated displacement and resorption. FIG. 1 shows the bands produced when the feed material is introduced intermittently. When the feed is continuous the sorbent material between the heaters may be wholly occupied by the sorbate. As chromatography proceeds, the sorbate is separated into four bands which are successively expelled through the outlet manifold 6 and diverted to collecting vessels by means not shown. FIG. 2 illustrates the displacement of the bands A to D from the outlet, band D being expelled first and band A last.

EXAMPLE 2

Referring now to FIG. 3, a mixture containing approximately equal amounts of heptane, octane, nonane, and decane (5ml.) is introduced on to one end of a straight column of coconut charcoal (Sutcliffe-Speakman 207c; 15g.). The column is maintained at a 110° C and a heater maintained at 500° C is passed along the length thereof, whilst nitrogen is passed through the column at a flow rate 100ml/min. The mixture is separated into fractions which are displaced from the column and detected. FIG. 3 shows a plot of the purity of the fractions against time.

EXAMPLE 3

Figure 4A:
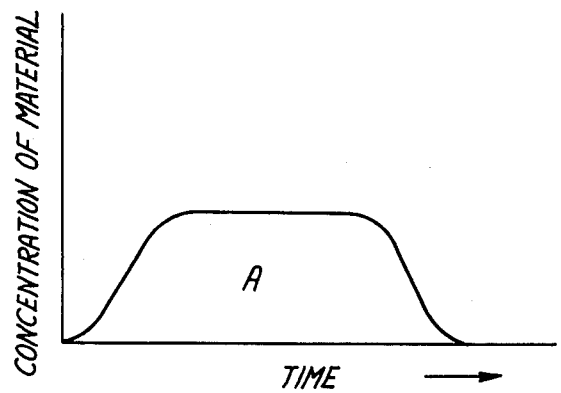
FIGS. 4a–4c show plots representing the catalytic conversion of a reactant into a product.
Figure 4B:
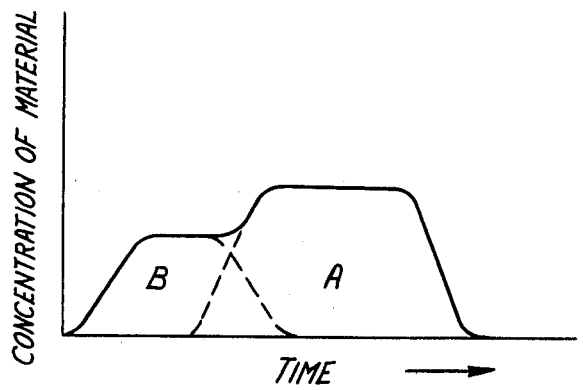
Figure 4C:
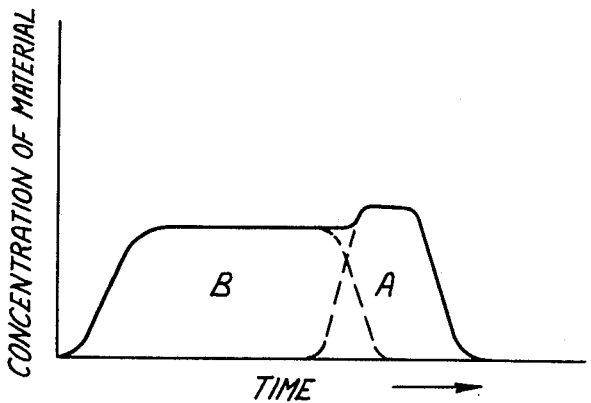

Referring now to FIGS. 4a–4c the apparatus shown in FIG. 1 is applied to the catalytic conversion of a reactant (A) into a product (B), the column being packed with catalytic sorbent material (not shown). As a heater approaches the reactant on the sorbent material catalytic conversion of the reactant is progressively effected into a product which is separated therefrom by displacement chromatography. In the steady state when conversion is complete each heater is associated with a band of sorbate undergoing repeated displacement and resorption. FIG. 4 shows at b the bands produced when the feed material is introduced intermittently or continuously. When the feed is continuous however the sorbent material between the heaters may be wholly occupied by the sorbate. As chromatography proceeds, conversion to the product is completed and the latter is expelled through the outlet manifold 6 and diverted to collecting vessels by means not shown. FIGS. 4a to 4c illustrate how the concentration of feed material (A) and product (B) vary as the sorbates pass through a section of the tube at different stages in the conversion process.

EXAMPLE 4

1,1,2-trichloroethane is introduced to one end of a column containing gamma alumina treated with potassium chloride at room temperature. A heater maintained at 500° C is passed along the column and the starting material is converted to 1, 1-dichloroethylene which emerges as the first organic product followed by trans-1, 2-dichloroethylene and cis-1, 2-dichloroethylene. It is also possible to arrange conditions such that hydrogen chloride produced by dehydrochlorination recombines with the olefines. Reaction with 1, 1-dichloroethylene yields a new product, 1, 1, 1-trichloroethane. Eventually large amounts of the latter product accumulate due to regeneration of the starting material by reaction also of the cis- and trans- isomers with hydrogen chloride followed by catalytic conversion.

EXAMPLE 5

A sample of n-hexane is introduced to one end of a column containing 0.6% Pt on gamma alumina (chlorinated at 300° C with $CCl_4$) maintained at room temperature. A heater maintained at 300° C is passed along the length thereof. In this case the 2 and 3-methyl pentanes initially produced remain nearer to the heated zone in the displacement sequence and when catalytic conversion of the n-hexane is completed, further isomerisation of the pentanes is effected by the heated zone to yield 2:2 and 2:3 - dimethyl butanes.

EXAMPLE 6

A sample of n-pentane is converted under the column conditions set out in Example 3 to isopentane.

EXAMPLE 7

A sample of 1-pentene is introduced to one end of a straight column containing gamma alumina treated with hydrogen fluoride at 150° C and operated at room temperature with a moving heater maintained at 250° C. A mixture of pentane isomers is produced with enrichment of trans-2-pentene.

I claim:

1. A chromatographic method for fractionating a mixture of sorbate components in a continuous operation comprising:

providing a flow path of sorbent having different affinities for the sorbate components of said mixture;

feeding said mixture into said flow path of sorbent; and thermally displacing a sorbate through said sorbent in advance of a substantially uniform heat zone of limited width to fractionate said sorbate components into an abutting succession of components in accordance with the affinities of said components for said sorbent by relative movement between the sorbent and the heat zone, the mixture being fractionated into sorbate components in the advancing relatively cool area of sorbent ahead of said heat zone, the amount of all sorbate components falling into said heat zone being relatively insignificant.

2. A method according to claim 1 in which the thermally displaced sorbate is one component of the mixture.

3. A method according to claim 1 further comprising passing a carrier gas through the sorbent material during operation of the method.

4. A method according to claim 1 in which the sorbent material comprises charcoal and the mixture comprises a plurality of saturated hydrocarbons.

5. A method according to claim 1 in which the sorbent material comprises $\gamma$ alumina and the mixture comprises a plurality of olefinically unsaturated or saturated hydrocarbons.

6. A method according to claim 1 further comprising adding a substance to the mixture to be fractionated, which substance is so chosen as to separate two components of the mixture on the sorbent material.

7. A method according to claim 1 in which the thermally displaced sorbate is unreactive and is so disposed in the displacement sequence as to separate a thermally labile sorbate in the mixture from the heated zone.

8. The chromatograhic method of claim 1 wherein the step of thermally displacing includes the step of continuously moving a plurality of spaced heat zones along the length of said flow path.

9. The chromatographic method of claim 1 wherein one of said sorbate components being displaced serves as a buffer as to at least one other sorbate component being displaced.

10. The chromatographic method of claim 9 wherein said buffer sorbate component is displaced directly ahead of said advancing heat zone.

* * * * *